(12) United States Patent
Noriki (10) Patent No.: US 9,395,366 B2
(45) Date of Patent: Jul. 19, 2016

(54) NON-HEATING DETECTION METHOD FOR DERMATOPHYTE

(71) Applicants: NATIONAL UNIVERSITY CORPORATION UNIVERSITY OF FUKUI, Fukui (JP); JNC CORPORATION, Tokyo (JP)

(72) Inventor: Sakon Noriki, Fukui (JP)

(73) Assignees: NATIONAL UNIVERSITY CORPORATION UNIVERSITY OF FUKUI, Fukui (JP); JNC CORPORATION, Tokyo (JP)

(*) Notice: Subject to any disclaimer, the term of this patent is extended or adjusted under 35 U.S.C. 154(b) by 0 days.

(21) Appl. No.: 14/598,621

(22) Filed: Jan. 16, 2015

(65) Prior Publication Data

US 2015/0132777 A1 May 14, 2015

Related U.S. Application Data

(62) Division of application No. 12/225,388, filed as application No. PCT/JP2007/055567 on Mar. 19, 2007, now Pat. No. 8,962,264.

(30) Foreign Application Priority Data

Mar. 20, 2006 (JP) .................................. 2006-077639

(51) Int. Cl.
*C12Q 1/00* (2006.01)
*C12Q 1/68* (2006.01)
(Continued)

(52) U.S. Cl.
CPC ...... *G01N 33/56961* (2013.01); *G01N 2333/37* (2013.01); *G01N 2800/20* (2013.01)

(58) Field of Classification Search
CPC .......... C12Q 1/00; C12Q 1/02; C12Q 1/6811; C12Q 1/6895; G01N 1/00; G01N 33/00; G01N 33/536; G01N 33/50; G01N 33/53; G01N 33/569; G01N 33/56961; G01N 33/577; G01N 2333/37; G01N 2469/00; G01N 2469/10
See application file for complete search history.

(56) References Cited

U.S. PATENT DOCUMENTS

2010/0068738 A1 3/2010 Kawamura et al.

FOREIGN PATENT DOCUMENTS

| EP | 0 970 966 | * | 1/2000 | ............. C07K 14/37 |
| JP | 2001-187750 | | 7/2001 | |

(Continued)

OTHER PUBLICATIONS

Extended European Search Report issued Apr. 1, 2010 in corresponding EP Patent Application No. 07739010.2.
(Continued)

*Primary Examiner* — Ja'na Hines
(74) *Attorney, Agent, or Firm* — Wenderoth, Lind & Ponack, L.L.P.

(57) ABSTRACT

The present invention provides a method of detecting dermatophyte, which does not require a complicated operation such as an enzyme treatment and a heat treatment.
The present invention provides a method of detecting dermatophyte, including a step of extracting a dermatophyte component from a sample with a treatment liquid containing a non-ionic surfactant or a zwitterionic surfactant, and a kit for diagnosing dermatophyte infection, containing a treatment liquid comprising the above surfactant, and an antibody specifically recognizing a dermatophyte component, which are housed in separate containers.

4 Claims, 4 Drawing Sheets

| No. 1 | 10%NP40 | No. 2 | 2% NP40 | |
| No. 3 | 5%DOC | No. 4 | 1%DOC | |
| No. 5 | 5%TRX | No. 6 | distilled water | heat treatment |
| No. 7 | 1%TRX | No. 8 | distilled water | stirring alone at room temperature |

(51) Int. Cl.
*G01N 33/53* (2006.01)
*G01N 33/567* (2006.01)
*G01N 33/569* (2006.01)

(56) References Cited

FOREIGN PATENT DOCUMENTS

| JP | 2002-148259 | | 5/2002 | | |
|---|---|---|---|---|---|
| JP | 2004-159593 | | 6/2004 | | |
| JP | 2004-258024 | | 9/2004 | | |
| JP | A-2004-159593 | * | 10/2004 | ............. | C12N 15/02 |
| WO | 94/10571 | | 5/1994 | | |
| WO | WO 94/10571 | * | 5/1994 | ............. | G01N 33/53 |

OTHER PUBLICATIONS

The Japanese Biochemical Society, "Shin Seikagaku Jikken Koza 1 Tanpakushitsu I-Bunri Seisei Seishitsu-", Tokyo Kagaku Dojin, Feb. 26, 1990, pp. 57-66.
Norio Uchiyama, "Treponema denticola no Chymotrypsin Protease ni Tsuite 1. Chushutsu Hoho no Kento", Nihon Univ. Dent. J., 1995, vol. 69, pp. 378-389, ISSN 0385-0102.
Nobel et al., American Family Physican., Jul. 1998, vol. 58(1), pp. 163-174.
Sueta et al., J Toxicol Sci., Dec. 1999, Suppl 2, pp. 1115-1128.
NCBI PubChem Compound website for "octyl-beta-D-glucoside", Compound Summary (CID 62852).

* cited by examiner

FIG. 1

No. 1  10%NP40
No. 2  2% NP40
No. 3  5%DOC
No. 4  1%DOC
No. 5  5%TRX
No. 6  distilled water — heat treatment
No. 7  1%TRX
No. 8  distilled water — stirring alone at room temperature

1 : blank
2 : 2%NP-40
3 : 5% CHAPS
4 : 1% CHAPS
5 : 5% DPC
6 : 1% DPC
7 : 5% Glucoside
8 : 1% Glucoside

NON-HEATING DETECTION METHOD FOR DERMATOPHYTE

TECHNICAL FIELD

The present invention relates to a non-heating detection method of dermatophyte, and to the diagnosis field of tinea.

BACKGROUND ART

Tinea, what is called athlete's foot, is dermatomycosis caused by infection of the skin with dermatophytes such as *Tricophyton rubrum* (hereinafter to be abbreviated as *T. rubrum*), *Tricophyton mentagrophytes* (hereinafter to be abbreviated as *T. mentagrophytes*), *Microsporum canis* (hereinafter to be abbreviated as *M. canis*), *Epidermophyton floccosum* (hereinafter to be abbreviated as *E. floccosum*) and the like. The main fungal infection site is interdigit of foot. However, genital, corpus and the like are also infected therewith, causing inflammation and intense pruritus in the infection site.

The diagnosis of tinea is mainly based on potassium hydroxide (KOH) direct microscopic examination including dissolving cornified layer obtained from the patient's skin with KOH and heat treatment, and microscopically observing hyphae. The microscopic examination requires considerable training, where difference between hypha and dust may be misjudged. While fungus itself can also be cultured and examined, it takes substantial time before the results are obtained.

It is often difficult to distinguish tinea from other diseases requiring different treatment methods such as eczema, dermatitis, pompholyx and the like. In fact, there is a report indicating that one-third of patients who visit dermatologists for "athlete's foot" as the chief complaint is affected with different diseases. Due to treatments based on such erroneous self-judgment, inflammation is frequently prolonged and may not cure.

As a detection method of athlete's foot, a dermatophyte infection site detection method using a copper sulfate solution is reported (see patent reference 1). This method enables detection in a short time at a low cost. However, as far as the present inventors have studied, no significant difference was found between healthy subjects and carrier subjects of tinea unguium.

The present inventor has produced an antibody against various tinea fungi (dermatophyte) antigens, found a method of specifically detecting tinea fungi (see patent references 2 and 3), whereby enabling convenient diagnosis of tinea fungi infection. However, since the method requires a heat treatment step irrespective of whether an enzyme treatment is involved, the detection is not always possible at any place. In addition, the method has a risk of burn and the like due to heating, posing a safety problem.

Accordingly, there is a demand for a convenient detection method of tinea fungi that does not require a complicated operation such as a heat treatment and the like.
patent reference 1: JP-A-2001-187750
patent reference 2: JP-A-2004-159593
patent reference 3: JP-A-2004-258024

DISCLOSURE OF THE INVENTION

Problems to be Solved by the Invention

It is an object of the present invention to provide a convenient and highly sensitive detection method of dermatophyte that does not require a complicated operation such as a heat treatment and the like. A further object of the present invention is to provide a kit for diagnosing dermatophyte infection, which can be utilized conveniently.

Means of Solving the Problems

The present inventor has first found that, even at room temperature, dermatophyte can be detected with sensitivity equivalent to that when a heat treatment is applied, by treating a sample with a non-ionic surfactant or a zwitterionic surfactant. Based on this finding, the present inventor has conducted intensive studies and completed the present invention.

Accordingly, the present invention provides the following.
[1] A method of detecting dermatophyte, comprising a step of extracting a dermatophyte component from a sample with a treatment liquid comprising a non-ionic surfactant or a zwitterionic surfactant.
[2] The method of the above-mentioned [1], wherein the non-ionic surfactant is polyoxyethylene alkylphenyl ether.
[3] The method of the above-mentioned [2], wherein the polyoxyethylene alkylphenyl ether is polyoxyethylene nonylphenyl ether.
[4] The method of the above-mentioned [1], wherein the non-ionic surfactant is alkyl glucoside.
[5] The method of the above-mentioned [4], wherein the alkyl glucoside is n-octyl-β-D-glucoside.
[6] The method of the above-mentioned [1], wherein the zwitterionic surfactant is alkyl betaine.
[7] The method of the above-mentioned [6], wherein the alkyl betaine is 3-[(3-cholamidopropyl)dimethyl-ammonio]propanesulfonate.
[8] The method of any one of the above-mentioned [1] to [7], wherein the dermatophyte is at least one kind selected from the group consisting of *Tricophyton rubrum*, *Tricophyton mentagrophytes*, *Microsporum canis* and *Epidermophyton floccosum*.
[9] A method of detecting dermatophyte, comprising the following steps:
(a) a step of extracting a dermatophyte component from a sample with a treatment liquid comprising a non-ionic surfactant or a zwitterionic surfactant,
(b) a step of forming a complex by contacting the dermatophyte component obtained in the above-mentioned step (a) with an antibody specifically recognizing the component, and
(c) a step of detecting the complex formed in the above-mentioned step (b).
[10] The method of the above-mentioned [9], wherein the non-ionic surfactant is polyoxyethylene alkylphenyl ether.
[11] The method of the above-mentioned [10], wherein the polyoxyethylene alkylphenyl ether is polyoxyethylene nonylphenyl ether.
[12] The method of the above-mentioned [9], wherein the non-ionic surfactant is alkyl glucoside.
[13] The method of the above-mentioned [12], wherein the alkyl glucoside is n-octyl-β-D-glucoside.
[14] The method of the above-mentioned [9], wherein the zwitterionic surfactant is alkyl betaine.
[15] The method of the above-mentioned [14], wherein the alkyl betaine is 3-[(3-cholamidopropyl)dimethyl-ammonio]propanesulfonate.
[16] The method of any one of the above-mentioned [9] to [15], wherein the antibody is produced by hybridoma 0014.
[17] A kit for diagnosing dermatophyte infection, comprising a treatment liquid comprising the surfactant of any one of the above-mentioned [1] to [7], and an antibody specifically recognizing a dermatophyte component, which are housed in separate containers.

Effect of the Invention

The method of detecting dermatophyte of the present invention enables a convenient, rapid and highly accurate detection of dermatophyte by utilizing the fact that dermatophyte components can be extracted without heating by using a non-ionic surfactant or a zwitterionic surfactant. Furthermore, the diagnosis kit of the present invention can be a tool suitable for the detection method of the present invention, and whether or not infected with dermatophyte can be diagnosed conveniently, rapidly and highly accurately.

BEST MODE FOR CARRYING OUT THE INVENTION

As the non-ionic surfactants in the present invention, known non-ionic surfactants can be used. Specifically, polyoxyethylene alkylphenyl ether, polyoxyethylene alkyl ether, sorbitan fatty acid ester, polyoxyethylene fatty acid ester, polyoxyethylene alkylamine, polyoxyethylene fatty acid bisphenyl, silicone or fluorine surfactants, polyoxyethylene castor oil, alkyl glucoside and the like can be mentioned. As these non-ionic surfactants, commercially available products can be preferably used.

In the present invention, polyoxyethylene alkylphenyl ether or alkyl glucoside is preferably used since they show a small influence on the antibody to be used, cause less denaturation of dermatophyte components, and can dominantly extract highly antigenic membrane components.

Examples of polyoxyethylene alkylphenyl ether include polyoxyethylene nonylphenyl ethers (e.g., NP-40; Nonidet P-40 (registered trade mark)), polyoxyethylene iso-octylphenyl ethers (e.g., Triton-X 100 (registered trade mark) (also abbreviated as TNX or TRX)) and the like. In view of the Example results, polyoxyethylene nonylphenyl ether is more preferable.

The average molecular weight of the non-ionic surfactants, particularly polyoxyethylene alkylphenyl ether, inter alia, polyoxyethylene nonylphenyl ether and polyoxyethylene iso-octylphenyl ether is not particularly limited. The molecular weight distribution of the above-mentioned non-ionic surfactants is not particularly limited, either.

The above-mentioned polyoxyethylene nonylphenyl ether is represented by, for example, the formula (1)

(1)

wherein m is generally 1-50, preferably 5-20, most preferably 8-12, and the nonyl group is preferably present at the 4-position.

Moreover, the above-mentioned polyoxyethylene iso-octylphenyl ether is represented by, for example, the formula (2)

(2)

wherein n is generally 1-50, preferably 5-20, most preferably 8-12, and the iso-octyl group is preferably present at the 4-position.

The carbon number of the alkyl moiety of alkyl glucoside is generally 6-20, preferably 7-18, most preferably 7-12. Examples of the alkyl glucoside include n-octyl-β-D-glucoside, n-octyl-β-D-maltoside, n-decyl-β-D-maltoside, n-decyl-β-D-maltoside, n-heptyl-β-D-thioglucoside, n-octyl-β-D-thioglucoside, n-nonyl-β-D-thiomaltoside and the like, preferably n-octyl-β-D-glucoside.

As the zwitterionic surfactant in the present invention, known zwitterionic surfactants can be used. Specific examples thereof include alkylamino fatty acid salt, alkyl betaine, alkylamine oxide and the like. As these zwitterionic surfactants, commercially available products can be preferably used.

In the present invention, alkyl betaine is preferably used since it shows a small influence on the antibody to be used, cause less denaturation of dermatophyte components, and can dominantly extract highly antigenic membrane components.

As the alkyl betaine, 3-[(3-cholamidopropyl)dimethyl-ammonio]propanesulfonate (CHAPS) is most preferable in view of the results of the Examples.

In the present invention, a dermatophyte component can be extracted from a sample by immersing the sample in a treatment liquid containing a non-ionic surfactant or a zwitterionic surfactant and the like.

The "treatment liquid" means a liquid that contains the aforementioned non-ionic surfactant or zwitterionic surfactant and is used for extracting a dermatophyte component from a sample. As the solvent, water is generally used. However, the solvent is not particularly limited as long as it does not inhibit antigen-antibody reactions. Furthermore, other solvents, additives (e.g., solubilizer, diluent, antigen activating agent) and the like may be added to a treatment liquid and reacted as long as the state of the dermatophyte component can be maintained and the extraction of the component can be facilitated. Examples of such additive include, but are not limited to, ethanol, methanol, phosphate buffer, formalin and the like. In addition, the concentration and amount of the additives and the like are not particularly limited as long as the necessary amount of the surfactant is ensured and the antigen-antibody reaction is not inhibited.

The concentration of the above-mentioned non-ionic surfactant in the above-mentioned treatment liquid is generally 0.1-10.0 wt %, preferably 1.0-5.0 wt %, more preferably 1.0-2.0 wt %. Particularly when the non-ionic surfactant is NP-40, the concentration is generally 0.1-10.0 wt %, preferably 1.0-5.0 wt %, more preferably 1.0-3.0 wt %. Particularly when the non-ionic surfactant is TNX, the concentration is generally 0.1-10.0 wt %, preferably 0.5-5.0 wt %, more preferably 0.5-2.0 wt %. In addition, particularly when the non-ionic surfactant is n-octyl-β-D-glucoside, the concentration is generally 0.01-10.0 wt %, preferably 0.5-5.0 wt %, more preferably 0.5-2.0 wt %.

The concentration of the above-mentioned zwitterionic surfactant in the above-mentioned treatment liquid is generally 0.01-10.0 wt %, preferably 0.5-5.0 wt %, more preferably. 0.5-2.0 wt %. Particularly when the zwitterionic surfactant is 3-[(3-cholamidopropyl)dimethyl-ammonio]propanesulfonate, the concentration is generally 0.01-10.0 wt %, preferably 0.5-5.0 wt %, more preferably 0.5-2.0 wt %.

The "sample" in the present invention is not particularly limited, and any sample suspected to contain dermatophyte can be used. Accordingly, the sample in the present invention can be one present in the living environment, one separated from a biological tissue and the like. Specific examples of the sample present in the living environment include floor coverings (e.g., carpet, bath mat, tatami etc.), footwear (e.g., shoes, slippers, sandals etc.), clothings (e.g., sock, is Japanese sock, stocking, underwear, headwear, bedding etc.), medical accessories (gauze, dressing, tweezers etc.), food, dust, mote, washing machine tub and the like. Examples of the samples separated from biological tissues (hereinafter to be referred to as biological sample) include skin, nail, scale, hair, pelage and the like. In the present invention, a biological sample is particularly preferable, and especially, a tissue rich in keratin substance to be a nutrient source of tinea fungi, and with high temperature and high humidity, which permits easy infection with tinea fungi and growth of tinea fungi therein is particularly preferable. Examples of the most preferable sample include skin (particularly foot interdigit region, groin, scale on scalp etc.), nail and the like.

The "dermatophyte" in the present invention generally means filamentous fungi that parasitize human skin, particularly causative fungi of tinea (hereinafter to be referred to as tinea fungi). The form and state of fungi may be any and include, for example, partial fungi fragments such as spore, hyphae, conidium and the like.

Examples of the species of dermatophyte include *T. rubrum, T. mentagrophytes, M. canis, E. floccosum, T. verrucosum, T. tonsurans, T. violaceum, T. equinum, T. glabrum, T. shoenleinii, M. gypseum, Arthroderma vanbreuseghemii, Arthroderma simii, Arthroderma benhamiae* and the like. Standard products of these species are available from American Type Culture Collection (ATCC), Institute for Fermentation, Osaka (IFO) and the like.

From among these, *T. rubrum, T. mentagrophytes, M. canis* and *E. floccosum* are preferably used as detection targets in the present invention. The reasons therefor are that the former two species make up 97% of tinea patients, and infection with the latter two species via pet animals is increasing.

The "dermatophyte component" in the present specification is not particularly limited as long as it is a substance constituting dermatophyte, and examples thereof include polysaccharides (e.g., chitin, chitosan, cellulose, glucan), protein, glycoprotein, peptide, phospholipid, low-molecular-weight compounds (e.g., steroid), nucleic acid and the like present in dermatophyte.

In the "step of extracting a dermatophyte component", a sample is, for example, added to or immersed in a treatment liquid comprising a non-ionic surfactant or a zwitterionic surfactant to extract a dermatophyte component.

The method of the present invention can be characteristically performed without a heat treatment. Accordingly, the temperature at the time of extraction only needs to be atmospheric temperature, namely, a temperature of the level not significantly preventing contact of a dermatophyte component with an antibody. The sample is treated at room temperature of generally about 4° C.-45° C., preferably about 10° C.-45° C. In addition, pH at the time of extraction is not particularly limited as long as it does not significantly prevent contact of a dermatophyte component with an antibody. It is generally 5.0-9.0, preferably 6.0-8.0. Furthermore, stirring is preferably performed to enhance the extraction efficiency.

In addition, the treatment time for extraction varies depending on whether the sample exists in the living environment or is a biological sample, the temperature and volume of the treatment liquid and the like. A longer treatment time is generally more preferable and it is preferably 1 min or more, more preferably 5 min or more, further preferably 10 min or more. When the non-ionic surfactant is NP-40, a longer treatment time is generally more preferable and it is preferably 1 min or more, more preferably 5 min or more, further preferably 10 min or more. When the non-ionic surfactant is n-octyl-β-D-glucoside, a longer treatment time is generally more preferable and it is preferably 1 min or more, more preferably 5 min or more, further preferably 10 min or more. When the zwitterionic surfactant is 3-[(3-cholamidopropyl)dimethyl-ammonio]propanesulfonate, a longer treatment time is generally more preferable and it is preferably 1 min or more, more preferably 5 min or more, further preferably 10 min or more.

After treating with the treatment liquid, a sample remaining in the resulting extract may or may not be separated. The separation operation can be performed according to a method known per se, such as centrifugation, filtration and the like. When the sample is not separated, the extract is left standing and the supernatant can be used.

Using the extract thus obtained as a specimen, the presence or absence of dermatophyte can be detected using the immunological technique described below.

In another aspect of the present invention, provided is a method of detecting dermatophyte, comprising the following steps:
(a) a step of extracting a dermatophyte component from a sample with a treatment liquid comprising a non-ionic surfactant or a zwitterionic surfactant,
(b) a step of forming a complex by contacting the dermatophyte component extracted in the above-mentioned step (a) with an antibody specifically recognizing the component, and
(c) a step of detecting the complex formed in the above-mentioned step (b).

In step (a), an operation in the same manner as in the above-mentioned "step of extracting a dermatophyte component" is performed to extract a dermatophyte component into a treatment liquid. The separation operation of the sample after extraction is preferably performed before step (b) or (c) mentioned below.

In step (b), a complex is formed by contacting the dermatophyte component obtained in step (a) with an antibody specifically recognizing the component.

The antibody specifically recognizing the dermatophyte component may be any of polyclonal antibody and monoclonal antibody. In addition, a fragment of antibody molecule such as $F(ab')_2$, Fab', or Fab fraction and the like can be used, and monoclonal antibody is desirably used. As these antibodies, antibodies prepared according to a method known per se and using dermatophytes as immunogen can be used. Such method is detailed in JP-A-2004-159593. Preferred are antibodies produced by hybridomas 0011 and 0014 described in JP-A-2004-159593 (hereinafter to be referred to as 0011 antibody and 0014 antibody), and more preferred is 0014 antibody in view of good reaction specificity to *T. rubrum, T. mentagrophytes, M. canis* and *E. floccosum*.

Furthermore, these antibodies may be directly or indirectly labeled with a labeling substance. Examples of the labeling substance include fluorescent substances (e.g., FITC, rhodamine), radioactive substances (e.g., $^{13}C$, $^3H$), enzymes (e.g., alkaline phosphatase, peroxidase) and colored particles (e.g., colloidal metal particles, colored latex).

The antibody-producing hybridoma 0014 was deposited at the International Patent Organism Depositary, National Institute of Advanced Industrial Science and Technology, AIST Tsukuba Central 6, 1-1, Higashi 1-chome Tsukuba-shi, Ibaraki-ken 305-8566 Japan on Oct. 8, 2002, and given Accession No. FERM P-19057.

Since 0011 antibody and 0014 antibody have reactivity with *T. rubrum, T. mentagrophytes, M. canis* and *E. floccosum*, which are the main causative fungi of tinea, the causative fungi of tinea can be comprehensively detected using only one of the antibodies. In addition, it is possible to identify the causative fungi of tinea by using one or more antibodies specifically recognizing a component derived from a single fungus (e.g., 0012 antibody, 0013 antibody and 0015 antibody described in JP-A-2004-258024).

The aforementioned "specifically recognizing" means that the antibody recognizes *T. rubrum, T. mentagrophytes, M. canis, E. floccosum* and the like and does not cross-react with other fungi such as *Aspergillus, Candida, Cryptococcus* and the like. Only one kind or two or more kinds of such antibodies may be used in this step.

While the above-mentioned "antibody specifically recognizing the dermatophyte component" can be used in the present invention in a soluble state and free of other binding, it is desirably bound to a solid phase. Examples of such "solid phase" include plates (e.g., microwell plate), tube, beads (e.g., plastic beads, magnetic beads), carriers for chromatography (e.g., Sepharose (trademark)), membranes (e.g., nitrocellulose membrane, PVDF membrane), gels (e.g., polyacrylamide gel) and the like. Among these, plates, beads and membranes are preferably used, and plates are most preferably used because of its handling convenience. Examples of the above-mentioned bond include, but are not particularly limited to, covalent bond, ionic bond, physical adsorption and the like. However, physical adsorption is preferable, since sufficient binding intensity can be obtained.

To suppress non-specific adsorption and non-specific reaction, a phosphate buffered solution of bovine serum albumin (BSA), cow milk protein and the like is contacted with the solid phase, and the solid phase surface uncoated with the antibody is generally blocked with the aforementioned BSA, cow milk protein etc.

The contact between an "antibody specifically recognizing the dermatophyte component" and the "dermatophyte component" in a sample in the present invention is not particularly limited as to the embodiment, order, specific method and the like, as long as the sample and the "antibody specifically recognizing the dermatophyte component" can interact with each other by being mixed in a reaction container. The contact is established by, for example, adding a sample to a plate on which an "antibody specifically recognizing the dermatophyte component" is solid phased.

The time period when such contact is maintained is not particularly limited as long as it is sufficient for the aforementioned antibody specifically recognizing the dermatophyte component and dermatophyte component in a sample to be bound to form a complex. It is several seconds to a dozen hours, preferably 5 min-10 hr, most preferably 30 min-2 hr. The temperature condition for the contact is room temperature of generally 4° C.-45° C., preferably 4° C.-37° C., most preferably about 15° C.-30° C. The pH condition at which the reaction is performed is preferably 5.0-9.0, particularly preferably 6.0-8.0.

In step (c), the "complex of the dermatophyte component and antibody specifically recognizing the dermatophyte component" formed in step (b) is detected.

The above-mentioned detection is performed by specifically detecting the "antibody specifically recognizing the dermatophyte component" contained in the complex.

For the detection, enzyme immunoassay (EIA), immunochromatography, latex agglutination, radioimmunoassay (RIA), fluorescent immunoassay (FIA), luminescence immunoassay, evanescent wave analysis and the like can be utilized. Among these, EIA and immunochromatography are preferable in view of the easiness of operation.

When EIA is selected as a detection method for step (c), EIA is preferably sandwich Enzyme-Linked ImmunoSorbent Assay (sandwich ELISA) using 2 kinds of "antibodies specifically recognizing the dermatophyte component". Since such sandwich ELISA uses 2 kinds of antibodies, it is superior in the specificity to the antigen.

As one kind of sandwich ELISA, there is a method which utilizes an avidin-biotin reaction. In this method, for example, a dermatophyte component in an extract is trapped by any solid-phased "antibody specifically recognizing the dermatophyte component", and an antigen-antibody reaction between the trapped dermatophyte component and the biotin-labeled "antibody specifically recognizing the dermatophyte component" are allowed to take place. Then, an enzyme-labeled streptavidin is added and an avidin-biotin reaction is then allowed to proceed. The dermatophyte component is detected by detecting this enzyme.

The biotin-labeled "antibody specifically recognizing the dermatophyte component" can be produced by linking biotin and the "antibody specifically recognizing the dermatophyte component" by a well-known method. For example, using a commercially available biotin labeling kit, biotin and the "antibody specifically recognizing the dermatophyte component" can be linked. As the enzyme-labeled streptavidin, a commercially available one can be preferably used.

In addition, sandwich ELISA utilizing an enzyme-labeled antibody is available. In this method, for example, a dermatophyte component in an extract is trapped by any solid-phased "antibody specifically recognizing the dermatophyte component", and an antigen-antibody reaction between the trapped dermatophyte component and the enzyme-labeled "antibody specifically recognizing the dermatophyte component" are allowed to take place. Then, the dermatophyte component is detected by detecting this enzyme.

The enzyme-labeled antibody can be produced by linking (labeling) the "antibody specifically recognizing the dermatophyte component" with an enzyme by a method known per se, for example, glutaraldehyde method, maleimide method and the like.

Examples of the "enzyme" of the enzyme-labeled streptavidin and enzyme-labeled antibody include peroxidase, alkaline phosphatase, glucose oxidase, β-galactosidase and the like.

The 2 kinds of "antibodies specifically recognizing the dermatophyte component" for performing sandwich ELISA may be any of monoclonal antibodies, polyclonal antibodies, and a combination of a monoclonal antibody and a polyclonal antibody.

As a substrate agent to be used for the detection of enzyme, a suitable agent is used according to the selected labeling enzyme. For example, when peroxidase is selected as an enzyme, o-phenylenediamine (OPD), tetramethyl benzidine benzidine (TMB) and the like are used, and when alkaline phosphatase is selected, p-nitrophenyl phosphate (PNPP) and the like are used. Similarly, as the reaction quenching liquid and the substrate dissolving liquid, conventionally known liquids can be appropriately used, without any particular limitation, according to the selected enzymes.

When immunochromatography is selected as a detection method for step (c), an extract is developed against an "antibody specifically recognizing the dermatophyte component" linearly solid-phased on a water-absorbing substrate such as nitrocellulose membrane and the like, from the under side of the membrane, to allow trapping of the dermatophyte component, and an antigen-antibody reaction between the trapped dermatophyte component and the labeled "antibody specifically recognizing the dermatophyte component" are allowed to take place. Then, the dermatophyte component is detected by a technique suitable for the label.

The 2 kinds of "antibodies specifically recognizing the dermatophyte component" for performing immunochromatography may also be any of monoclonal antibodies, polyclonal antibodies, and a combination of a monoclonal antibody and a polyclonal antibody.

As one specific example, when a biological sample is subjected to ELISA, for example, the skin or nail of a tinea patient is immersed in the above-mentioned treatment liquid, and the mixture is stirred at room temperature for a given time to extract a dermatophyte component. The extract is then dispensed to a microplate on which any "antibody specifically recognizing the dermatophyte component" has been solid-phased, and left to stand at room temperature for a given time. The plate is washed to remove unreacted antigen, and a solution of the above-mentioned biotinylated antibody is dispensed to the plate and left to stand for a given time to form a complex. The plate is further washed to remove unreacted antibody, and then a peroxidase-labeled streptavidin solution is dispensed to the plate and allowed to react at room temperature for a given time. The plate is washed, and then the complex is detected through a reaction with a chromogenic substrate (e.g., TMB etc.) solution. A sample showing coloring after reaction with TMB solution is judged to contain tinea fungi.

When a sample present in the living environment is subjected to ELISA, for example, a part of a floor covering or clothing suspected to contain tinea fungus is immersed in the above-mentioned treatment liquid, the mixture is stirred at room temperature for a given time, and a dermatophyte component is extracted. The tinea fungus is detected by subjecting the extract to an operation similar to the above.

As another specific example, when the above-mentioned sample is subjected to immunochromatography, a test piece is immersed in an extract to allow development. The test piece consists of a strip-shaped antibody solid-phased support; a particle-labeled material holding carrier and a liquid sample absorption carrier comprised of filter paper, which are laminated on the lower end of the support via one end; and a water-absorbing carrier comprised of filter paper, which is laminated on the upper end of the aforementioned antibody solid-phased support via one end. In the above-mentioned antibody solid-phased support, an "antibody specifically recognizing the dermatophyte component" that reacts with a dermatophyte component (antigen-antibody reaction) is solid-phased on a nitrocellulose sheet. The solid phase is formed by applying the above-mentioned antibody solution onto the nitrocellulose sheet and drying the solution. The solid-phased antibody specifically recognizes the dermatophyte component in the extract developed and can trap a complex of the component and the particle-labeled antibody mentioned above. Accordingly, when the "antibody specifically recognizing the dermatophyte component" is linearly solid-phased on the antibody solid-phased support, the line is colored by the particulate label, enabling judgment of the presence of tinea fungi.

The present invention also provides a kit for diagnosing dermatophyte infection, housing the above-mentioned treatment liquid comprising a non-ionic surfactant or a zwitterionic surfactant, and an antibody specifically recognizing the dermatophyte component in separate containers.

The antibody may be housed in the container in the form of an antibody solution, or solid-phased on a plate (e.g., used for ELISA), or applied to a support (e.g., used for immunochromatography).

The kit may contain, besides a treatment liquid comprising a non-ionic surfactant or a zwitterionic surfactant, and an antibody specifically recognizing the dermatophyte component, a reagent and the like. Examples of the reagent and the like include a buffer for diluting the treatment liquid or antibody, a labeling substance (e.g., fluorescent dye, enzyme), a reaction container, a positive control, a negative control, an instruction with the description of examination protocols and the like. These elements may also be previously mixed as necessary. Using the kit, the diagnosis of dermatophyte infection can be facilitated.

EXAMPLES

The present invention is explained in more detail in the following by referring to Examples, which are not to be construed as limitative. The present invention can be variously modified without departing from the technical idea of the invention.

Example 1

Preparation of Sample

As the surfactants, sodium deoxycholate (hereinafter DOC), which is an anionic surfactant, and NP-40 (polyoxyethylene nonylphenyl ether) and TNX (polyoxyethylene isooctylphenyl ether), which are non-ionic surfactants, were used.

5 wt % and 1 wt % aqueous solutions were prepared for DOC, wt % and 2 wt % aqueous solutions were prepared for NP-40, and 5 wt % and 1 wt % aqueous solutions were prepared for TNX. A nail from a tinea unguium patient definitively diagnosed by the KOH method was divided into 8 almost equivalent amounts. Six out of 8 nails were each placed in an aqueous surfactant solution (300 μl), and the mixture was stirred at room temperature (about 20° C.) for 20 min. As one control, one nail was placed in 300 μl of distilled water, and the mixture was stirred at room temperature (about 20° C.) for 20 min. For the other control, one nail was placed in 300 μl of distilled water, and the mixture was subjected to a heat treatment by placing it on boiling water for 10 min. After the heat treatment, the mixture was allowed to cool to room temperature and used as a sample.

Example 2

Detection of Tinea Fungi by Tinea Fungi Diagnosis Strip Test

From the samples after each treatment, 120 μl was applied to a test piece for a tinea fungi diagnosis strip test produced using the 0014 antibody. The specific method is as follows.

1) Production of Antibody Solid-Phased Support

To produce an antibody solid-phased support on which the 0014 antibody has been linearly solid-phased, a nitrocellulose sheet (Millipore, HiFlow Plus) was cut into 5 mm×20 mm, and the 0014 antibody solution was applied to the sheet at 10 mm from the lower end with BioJet Q3000 (Biodot), and dried at room temperature for 2 hr.

2) Preparation of Colloidal Gold Particle-Labeled Material Holding Carrier a. Colloidal Gold Particle-Labeled 0014 Antibody To a dispersion (100 mL) of colloidal gold having a particle size of 40 nm, which was adjusted to pH6.0 with 0.1% $K_2CO_3$ solution was added a monoclonal antibody 0014 solution (400 μg), and the mixture was admixed at room temperature. Then the mixture was blended with 0.1% bovine serum albumin solution, and centrifuged at 6000 rpm for 20 min. The precipitate was re-suspended in PBS containing 0.1% bovine is serum albumin solution to give colloidal gold particle-labeled 0014 antibody solution.

b. Colloidal Gold Particle-Labeled Material Holding Carrier

A glass fiber non-woven fabric (Millipore, GFCP001050, 5 mm×10 mm) was impregnated with 25 µL of the above-mentioned colloidal gold particle-labeled antibody and dried by ventilation.

3) Production of Immunochromatography Test Piece

A colloidal gold-labeled material holding carrier was placed on an antibody solid-phased support up to 2.5 mm from the lower end thereof. Further, a liquid sample absorption carrier (3MM Chr, Whatman) was placed on the colloidal gold-labeled material holding carrier up to 2.5 mm from the lower end thereof. In addition, a water-absorbing carrier (3MM Chr, Whatman) was placed on the antibody solid-phased support up to 2 mm from the upper end thereof, and a transparent tape was finally attached to the top and fixed thereon to give an immunochromatography test piece.

Figure 1:
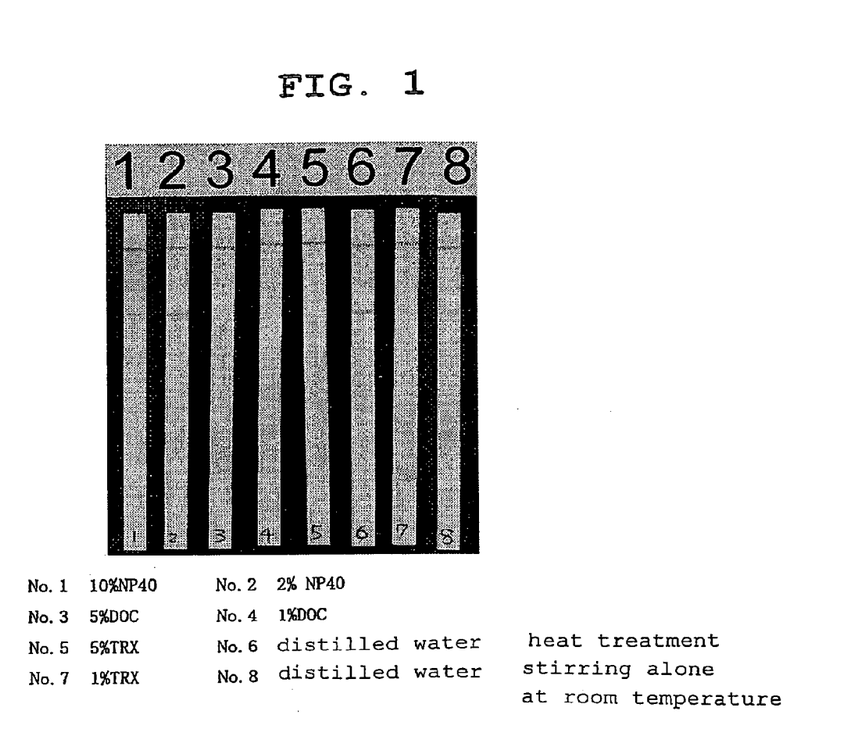
FIG. 1 shows the results of tinea fungi diagnosis strip tests using various surfactants.
Figure 2:
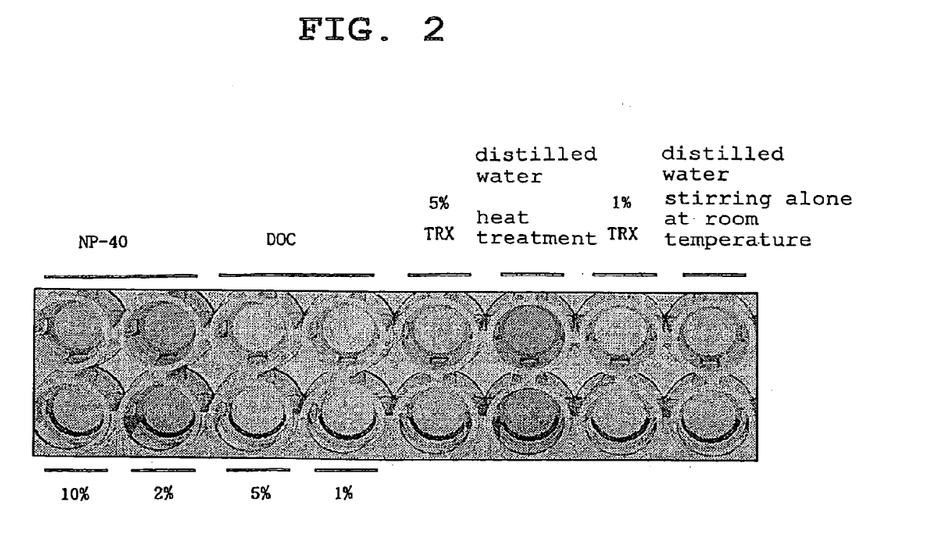
FIG. 2 shows the results of tinea fungi infection diagnoses by ELISA using various surfactants.

A strip test was performed using the above-mentioned test piece by developing the sample. The visual judgment results after 5 min are shown in FIG. 1. The line indicating the presence of tinea fungi appeared when a non-ionic surfactant was used, which established that the antigen can be extracted with a surfactant. The line did not appear when anionic DOC was used. When the specimen contains many tinea fungi such as tinea unguium, tinea fungi could be detected with 0014 antibody even by simply stirring the sample in water.

Example 3

Detection of Antigen by ELISA

A treatment liquid sample similar to that prepared in Example 1 was measured by ELISA. The method was as follows.
1) solid phasing of antibody: The 0014 antibody was diluted with 50 mM carbonate buffer (pH 9.6) to a concentration of 20 dispensed to each well of a 96 well microplate (#9018, Corning Incorporated) by 50 µl, and incubated overnight at 4° C.
2) blocking: An aqueous Yukijirushi BlockAce 25% solution was prepared, dispensed by 300 µl, and incubated at room temperature for 1 hr.
3) washing: PBS containing 0.05% Tween 20 (Nacalai Tesque) was dispensed by 300 µl, and washed by repeating stirring and discarding 3 times.
4) antigen-antibody reaction with sample: A sample was added to each well by 50 µl and the mixture was incubate at room temperature for 1 hr.
5) The washing operation similar to the above-mentioned 3) was performed 3 times.
6) A biotinylated 0014 antibody was diluted to 1 µg/ml with 10% aqueous BlockAce solution, dispensed to each well by 50 µl, and incubated for 1 hr.
7) The washing operation similar to the above-mentioned 3) was performed 3 times.
8) A peroxidase-labeled streptavidin liquid (KPL) was diluted 2000-fold with 10% BlockAce, dispensed to each well by 50 µl, and incubated for 30 min.
9) The washing operation of the above-mentioned 3) was performed 4 times.
10) A TMB chromogen liquid (DAKO) was dispensed to each well by 50 µl, and reacted under shading for 10 min.
11) The reaction was quenched by dispensing 1N sulfuric acid by 50 µl.
12) The absorbance (OD) was measured by a microtiter plate reader at main-wavelength 450 nm, sub-wavelength 650 nm.

The results are shown in Table 1. Like the strip test, the results equivalent to those obtained by the heat treatment were obtained even by a non-ionic surfactant treatment at room temperature.

TABLE 1

| OD value | | | | | | | |
|---|---|---|---|---|---|---|---|
| NP-40 | | DOC | | 5% distilled water heat | | 1% | stirring alone in distilled water at room |
| 10% | 2% | 5% | 1% | TRX | treatment | TRX | temperature |
| 0.447 | 1.660 | 0.026 | 0.027 | 0.431 | 2.635 | 0.138 | 0.447 |
| 0.492 | 1.806 | 0.023 | 0.024 | 0.424 | 2.753 | 0.153 | 0.417 |

% means wt %.

Example 4

Comparison with Heat Treatment in Strip Test

To compare with the heat treatment, 5 nail samples from tinea fungi patients and 5 nail samples from healthy subjects were subjected to a heat treatment and a 2 wt % NP-40 treatment at room temperature, and examined by a strip test.

Figure 3:
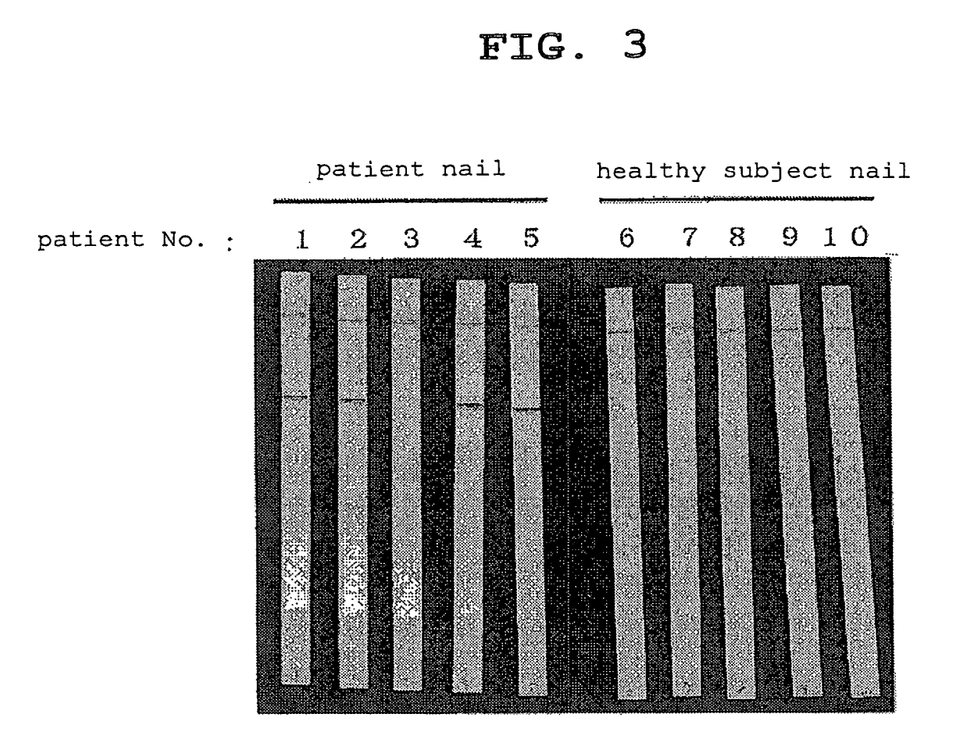
FIG. 3 shows the results of tinea fungi diagnosis strip tests by a heat treatment in distilled water.
Figure 4:
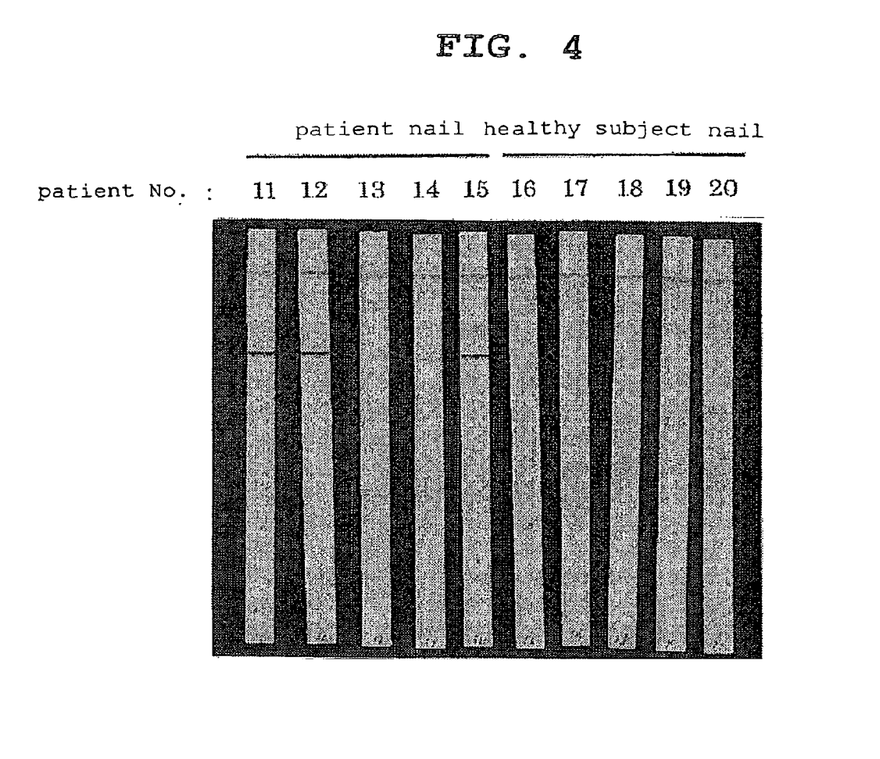
FIG. 4 shows the results of tinea fungi diagnosis strip tests by a 2% NP-40 treatment at room temperature.
Figure 5:
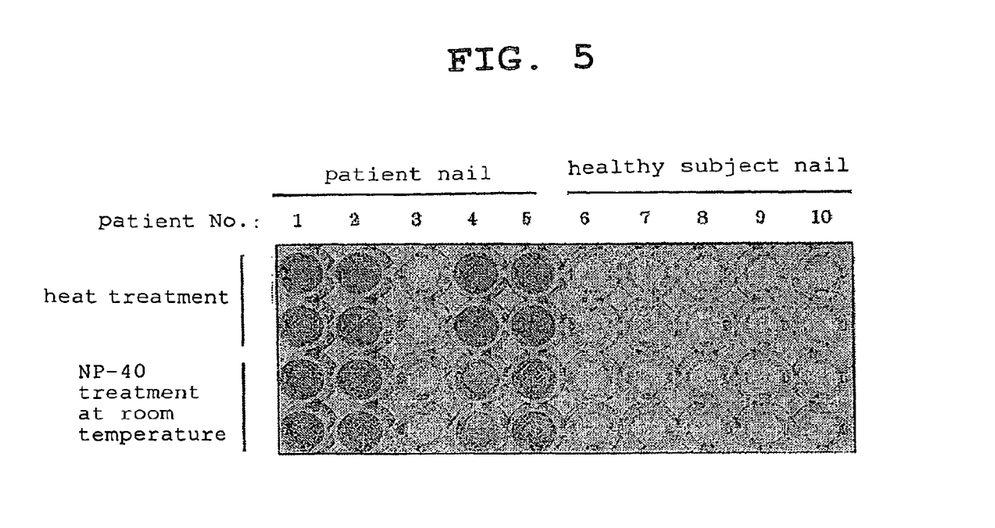
FIG. 5 shows the results of tinea fungi infection diagnoses by ELISA with or without a heat treatment.

The results are shown in FIG. 3 and FIG. 4. In patient No. 1 (Nos. 1 and 11), 2 (Nos. 2 and 12), 4 (Nos. 4 and 13) and 5 (Nos. 5 and 15), the line appeared by both the heat treatment and NP-40 treatment. In patient No. 3 (Nos. 3 and 13), the line did not appear by both the heat treatment and NP-40•treatment. In healthy subject nail (Nos. 6-10, 16-20), the line did not appear by both the heat treatment and NP-40 treatment.

Example 5

Comparison with Heat Treatment in ELISA

To compare with the heat treatment, 5 nail samples from tinea fungi patients and 5 nail samples from healthy subjects were subjected to a heat treatment and a 2 wt % NP-40 treatment at room temperature in the same manner as in Example 4, and examined by ELISA. ELISA was performed according to a method same as in Example 3.

The results are shown in Table 2. The heat treatment and NP-40 treatment at room temperature of patient Nos. 1, 2, 3, 4 and 5 produced almost the same results. The somewhat lower value in NP-40 of No. 4 is considered to be attributable to the difference in the amount of distributed nail or in the amount of tinea fungi contained in the nail. The OD value of patient No. 3 without the line in the strip test was about 0.020, suggesting the presence of a slight amount of tinea fungi antigen, which is considered to be not more than the sensitivity level in the strip test. In the healthy subjects, results obtained were all negative in both the heat treatment and the NP-40 treatment at room temperature, and false-positive was not observed either.

TABLE 2

| | OD value | | | | | | | | | |
|---|---|---|---|---|---|---|---|---|---|---|
| patient | Patient nail | | | | | healthy subject nail | | | | |
| No. | 1 | 2 | 3 | 4 | 5 | 6 | 7 | 8 | 9 | 10 |
| heat | 3.529 | 3.520 | 0.022 | 3.642 | 3.649 | 0.001 | 0.015 | 0.002 | 0.002 | 0.003 |
| treatment | 3.638 | 3.338 | 0.023 | 3.690 | 3.770 | 0.004 | 0.000 | 0.001 | 0.003 | 0.001 |

TABLE 2-continued

| patient | Patient nail | | | | | healthy subject nail | | | | |
|---|---|---|---|---|---|---|---|---|---|---|
| No. | 1 | 2 | 3 | 4 | 5 | 6 | 7 | 8 | 9 | 10 |
| NP-40 treatment at room temperature | 3.609 3.512 | 3.559 3.357 | 0.019 0.020 | 1.182 1.174 | 3.283 3.386 | 0.002 0.000 | 0.002 0.000 | 0.001 0.001 | 0.002 0.000 | 0.000 0.000 |

As the reason for the failure to obtain positive results in No. 3 patient, there is a possibility that the nail used for the diagnosis of the tinea fungi patient contained tinea fungi but the nail used in the Example did not, since the nail used for the diagnosis and the nail used in the Example were not the same.

Example 6

Detection of Antigen by ELISA Using Various Surfactants

The following 3 surfactants were examined:

1. zwitterionic surfactant: 3-[(3-cholamidopropyl)dimethyl-ammonio]propanesulfonate (CHAPS)
2. cationic surfactant: 1-dodecylpyridinium chloride (DPC)
3. non-ionic surfactant: n-octyl-β-D-glucoside (Glucoside)

Solutions having a concentration of 1% (w/v) and 5% (w/v) were prepared for each surfactant. As a positive control, 2% NP-40 was used. The nail of a tinea unguium patient (Case 29) was divided into 7 almost equivalent amounts, placed in respective solutions and stirred for 20 min. Thereafter, the antigen amount was measured by ELISA. ELISA was performed according to a method same as in Example 3.

Figure 6:
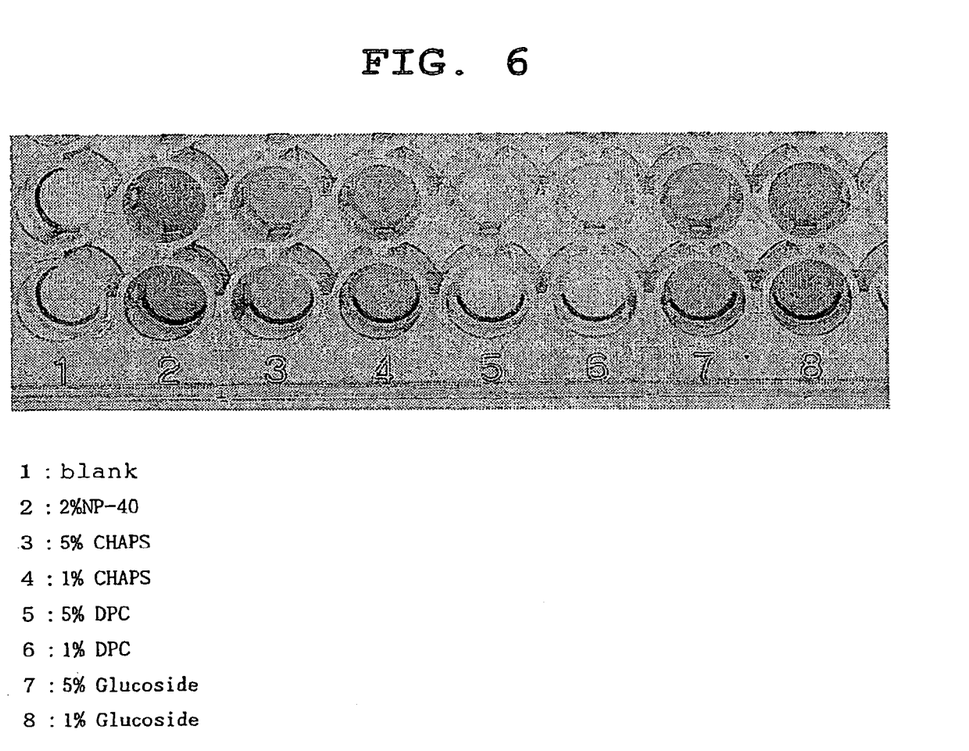
FIG. 6 shows the results of tinea fungi infection diagnoses by ELISA using various surfactants.

The results are shown in FIG. 6. Using the non-ionic surfactant Glucoside, good detection sensitivity next to NP-40 could be obtained, and positive results could be obtained even with a zwitterionic surfactant CHAPS. However, an ionic surfactant DPC could not detect dermatophyte.

INDUSTRIAL APPLICABILITY

According to the present invention, dermatophyte can be detected with sensitivity equivalent to that achieved by a heat treatment, by a treatment with a particular surfactant. Therefore, dermatophyte can be safely detected without a complicated step.

This application is based on a patent application No. 2006-077639 filed in Japan (filing date: Mar. 20, 2006), the contents of which are incorporated in full herein by this reference.

The invention claimed is:

1. A method of detecting dermatophyte, comprising the following steps:
    (a) a step of extracting a dermatophyte component from a sample selected from group consisting of skin, nail, scale, hair and pelage with a treatment liquid comprising 0.5-5.0 wt % of n-octyl-β-D-glucoside at a temperature of 4° C.-45° C.,
    (b) a step of forming a complex by contacting the dermatophyte component obtained in said step (a) with an antibody produced by hybridoma 0014, and
    (c) a step of detecting the complex formed in said step (b).
2. The method of claim 1, wherein the treatment liquid comprises 0.5-2.0 wt % of n-octyl-β-D-glucoside.
3. A kit for diagnosing dermatophyte infection, comprising a treatment liquid comprising 0.5-5.0 wt % of n octyl-β-D-glucoside and an antibody produced by hybridoma 0014, which are housed in separate containers.
4. The kit for diagnosing dermatophyte infection according to claim 3, wherein the treatment liquid comprises 0.5-2.0 wt % of n-octyl-β-D-glucoside.

* * * * *